(12) United States Patent
Pomeranz (10) Patent No.: US 8,998,926 B2
(45) Date of Patent: Apr. 7, 2015

(54) HEAT DETACHABLE COIL

(75) Inventor: Mark L. Pomeranz, Bernardsville, NJ (US)

(73) Assignee: Depuy Synthes Products, LLC, Raynham, MA (US)

( * ) Notice: Subject to any disclaimer, the term of this patent is extended or adjusted under 35 U.S.C. 154(b) by 1367 days.

(21) Appl. No.: 11/688,172

(22) Filed: Mar. 19, 2007

(65) Prior Publication Data
US 2007/0239196 A1 Oct. 11, 2007

Related U.S. Application Data

(60) Provisional application No. 60/789,777, filed on Apr. 6, 2006.

(51) Int. Cl.
*A61F 11/00* (2006.01)
*A61B 17/12* (2006.01)

(52) U.S. Cl.
CPC ....... *A61B 17/12022* (2013.01); *A61B 17/1214* (2013.01); *A61B 2017/12068* (2013.01)

(58) Field of Classification Search
CPC ................ A61B 17/12022; A61B 17/1214; A61B 2017/12068; A61B 2017/1209
USPC ............. 604/93.01, 95.05, 113; 606/200, 195
See application file for complete search history.

(56) References Cited

U.S. PATENT DOCUMENTS

| | | | |
|---|---|---|---|
| 4,346,712 A * | 8/1982 | Handa et al. | 606/195 |
| 4,735,201 A | 4/1988 | O'Reilly | |
| 5,108,407 A | 4/1992 | Geremia et al. | |
| 5,122,136 A | 6/1992 | Guglielmi et al. | |
| 5,334,210 A | 8/1994 | Gianturco | |
| 5,350,397 A | 9/1994 | Palermo et al. | |
| 5,382,259 A | 1/1995 | Phelps et al. | |
| 5,759,161 A | 6/1998 | Ogawa et al. | |
| 5,855,578 A | 1/1999 | Guglielmi et al. | |
| 5,911,737 A | 6/1999 | Lee et al. | |
| 5,941,888 A * | 8/1999 | Wallace et al. | 606/108 |
| 5,944,733 A | 8/1999 | Engelson | |
| 6,010,498 A | 1/2000 | Guglielmi | |
| 6,113,622 A | 9/2000 | Hieshima | |

(Continued)

FOREIGN PATENT DOCUMENTS

EP 0830873 A2 3/1998
EP 0830873 A3 4/1998

(Continued)

OTHER PUBLICATIONS

Hot Melt Adhesives Defined—Hot Melt Adhesives Technology Review Website printout—circa 1999.

(Continued)

*Primary Examiner* — Darwin Erezo
*Assistant Examiner* — Sidharth Kapoor
(74) *Attorney, Agent, or Firm* — Cook Alex Ltd.

(57) ABSTRACT

An embolic coil deployment system for placing a coil at a preselected site within a vessel of the human body is provided. The deployment system includes a heating element at the distal end of a detachment member and a heat-responsive coupling attached to a delivery member for holding the coil during positioning of the coil. The heating element is heated to reduce the strength of and sever the heat-responsive coupling for releasing the coil at a desired position within the body vessel.

22 Claims, 3 Drawing Sheets

(56) References Cited

U.S. PATENT DOCUMENTS

| | | | |
|---|---|---|---|
| 6,221,066 | B1 | 4/2001 | Ferrera et al. |
| 6,277,126 | B1 * | 8/2001 | Barry et al. .................... 606/108 |
| 6,296,622 | B1 * | 10/2001 | Kurz et al. ................. 604/93.01 |
| 6,371,972 | B1 | 4/2002 | Wallace et al. |
| 6,478,773 | B1 * | 11/2002 | Gandhi et al. ................ 604/113 |
| 6,533,801 | B2 | 3/2003 | Wallace et al. |
| 6,623,493 | B2 | 9/2003 | Wallace et al. |
| 6,692,483 | B2 | 2/2004 | Vardi et al. |
| 6,743,236 | B2 | 6/2004 | Barry et al. |
| 6,884,257 | B1 * | 4/2005 | Cox ............................ 623/1.11 |
| 7,179,276 | B2 | 2/2007 | Barry et al. |
| 2001/0009996 | A1 | 7/2001 | Ferrera et al. |
| 2001/0056281 | A1 | 12/2001 | Wallace et al. |
| 2003/0163189 | A1 * | 8/2003 | Thompson et al. .......... 623/1.11 |
| 2004/0225279 | A1 | 11/2004 | Raymond |
| 2005/0021023 | A1 | 1/2005 | Guglielmi et al. |

FOREIGN PATENT DOCUMENTS

| | | |
|---|---|---|
| EP | 0992219 | 4/2000 |
| EP | 1120088 | 8/2001 |
| WO | WO/93/16650 | 9/1993 |
| WO | WO 97/01368 | 1/1997 |

OTHER PUBLICATIONS

Adhesive, 3M® JET-MELT™ website printouts—circa 1995.
Notification of Transmittal of the International Search Report and the Written Opinion of the International Searching Authority, dated Sep. 10, 2008 in PCT/US07/07878.
Notification Concerning Transmittal of International Preliminary Report on Patentability and Written Opinion of the International Searching Authority, dated Sep. 10, 2008 in PCT/US07/07878.
Extended European Search Report with Supplementary European Search Report and European Search Opinion, EP 07774201.3(EP2001543), Feb. 15, 2010.

* cited by examiner

HEAT DETACHABLE COIL

CROSS-REFERENCE TO RELATED APPLICATION

This claims priority from provisional patent application Ser. No. 60/789,777, filed Apr. 6, 2006.

BACKGROUND OF THE INVENTION

1. Field of the Invention

The present invention relates to a medical device for placing an embolic coil at a preselected location within a vessel of the human body, and more particularly, relates to a flexible delivery member having a heating element and a heat-responsive coupling member at the distal tip of the delivery member for holding the embolic coil in order to transport the coil to a desired position within the vessel and release the embolic coil at that position.

2. Description of the Prior Art

For many years flexible catheters have been used to place various devices within the vessels of the human body. Such devices include dilatation balloons, radiopaque fluids, liquid medications and various types of occlusion devices such as balloons and embolic coils. Examples of such catheter devices are disclosed in U.S. Pat. No. 5,108,407, entitled "Method and Apparatus for Placement of an Embolic Coil"; and U.S. Pat. No. 5,122,136, entitled "Endovascular Electrolytically Detachable Guidewire Tip for the Electroformation of Thrombus in Arteries, Veins, Aneurysms, Vascular Malformations and Arteriovenous Fistulas." These patents disclose devices for delivering embolic coils to preselected positions within vessel of the human body in order to treat aneurysms, or alternatively, to occlude the blood vessel at the particular location.

Coils which are placed in vessels may take the form of helically wound coils, or alternatively, may be random wound coils, coils wound within other coils or many other such configurations. Examples of various coil configurations are disclosed in U.S. Pat. No. 5,334,210, entitled "Vascular Occlusion Assembly; and U.S. Pat. No. 5,382,259, entitled "Vasoocclusion Coil with Attached Tubular Woven or Braided Fibrous Coverings." Embolic coils are generally formed of radiopaque metallic materials, such as platinum, gold, tungsten, or alloys of these metals. Often times, several coils are placed at a given location in order to occlude the flow of blood through the vessel by promoting thrombus formation at the particular location.

In the past, embolic coils have been placed within the distal end of the catheter. When the distal end of the catheter is properly positioned the coil may then be pushed out of the end of the catheter with, for example, a guidewire to release the coil at the desired location. This procedure of placement of the embolic coil is conducted under fluoroscopic visualization such that the movement of the coil through the vasculature of the body may be monitored and the coil may be placed at the desired location. With these placement systems there is very little control over the exact placement of the coil inasmuch as the coil may be ejected to a position some distance beyond the end of the catheter.

Numerous procedures have been developed to enable more accurate positioning of coils within a vessel. Still another such procedure involves the use of a glue, or solder, for attaching the embolic coil to a guidewire which, is in turn, placed within a flexible catheter for positioning the coil within the vessel at a preselected position. Once the coil is at the desired position, the coil is restrained by the catheter and the guidewire is pulled from the proximal end of the catheter to thereby cause the coil to become detached from the guidewire and released from the catheter system Such a coil positioning system is disclosed in U.S. Pat. No. 5,263,964, entitled "Coaxial Traction Detachment Apparatus and Method."

Another coil positioning system utilizes a catheter having a socket at the distal end of the catheter for retaining a ball which is bonded to the proximal end of the coil. The ball, which is larger in diameter than the outside diameter of the coil, is placed in a socket within the lumen at the distal end of the catheter and the catheter is then moved into a vessel in order to place the coil at a desired position. Once the position is reached, a pusher wire with a piston at the end thereof is pushed distally from the proximal end of the catheter to thereby push the ball out of the socket in order to release the coil at the desired position. Such a system is disclosed in U.S. Pat. No. 5,350,397, entitled "Axially Detachable Embolic Coil Assembly." One problem with this type of coil placement system which utilizes a pusher wire which extends through the entire length of the catheter and which is sufficiently stiff to push an attachment ball out of engagement with the socket at the distal end of the catheter is that the pusher wire inherently causes the catheter to be very stiff with the result that it is very difficult to guide the catheter through the vasculature of the body.

Another method for placing an embolic coil is that of utilizing a heat releasable adhesive bond for retaining the coil at the distal end of the catheter. One such system uses laser energy which is transmitted through a fiber optic cable in order to apply heat to the adhesive bond in order to release the coil from the end of the catheter. Such a method is disclosed in U.S. Pat. No. 5,108,407, entitled "Method and Apparatus for Placement of an Embolic Coil." Such a system also suffers from the problem of having a separate, relatively stiff element which extends throughout the length of the catheter with resulting stiffness of the catheter.

Still another method for placing an embolic coil is disclosed in U.S. Pat. No. 6,113,622, entitled "Embolic Coil Hydraulic Deployment System." This patent discloses the use of fluid pressure which is applied to the distal tip of the catheter for expanding the lumen of the catheter in order to release the embolic coil. Further approaches are found in U S. Pat. No. 6,277,126, No. 6,743,236 and No. 7,179,276, entitled "Heated Vascular Occlusion Coil Deployment System." These concern embolic coil deployment systems that include an energy-imparting element at the distal end of a delivery member along with an energy-responsive coupling member that releases the coil upon application of energy.

Each of the patents and references noted herein are hereby incorporated by reference hereinto. There still remains a need for a coil release mechanism and system and method that have members for delivery of the coil to the proper position. In addition, with some embodiments of the present disclosure, it has been determined that guidance provided by properly located radiopaque members assists in locating the condition at which the system is properly arranged for coil deployment upon application of energy.

SUMMARY OF THE INVENTION

The present invention is directed toward an aspect or embodiment of a vascular occlusion coil deployment system for use in placing an embolic coil at a preselected site within a vessel which includes an elongated flexible delivery member having a lumen extending therethrough. An elongated flexible detachment member having a lumen extending therethrough is slidably positioned within the lumen of the delivery member. An energy-application element such as a heating element is affixed to the distal end of the detachment member, and an energy-activated coupling member joins an embolic coil to the delivery member.

In some embodiments, at least one marker is positioned along the detachment member at a suitable location which can be in a distal portion thereof. In such embodiments, at least one marker is positioned along the delivery member at a suitable location that is coordinated with the location of the detachment member marker. The respective marker locations are coordinated so that they are in alignment (such as when viewed with equipment to detect radiopaque markings) when the energy-application element is in general radial alignment with the energy-activated coupling, such alignment being achieved by relative slidable movement between the energy-application element and the energy-activated coupling.

The energy-application element is adapted to be coupled to a source of energy through an energy transmission conductor, which typically extends through the lumen in the detachment member. The energy-activated coupling member that bonds the delivery member to the embolic coil exhibits the characteristic of softening, yielding and severing upon being subjected to adequate energy, such as when heated to a desired temperature. When energy is thus applied through the conductor to the heating element, the embolic coil is thereby released at a preselected site.

In accordance with another embodiment or aspect of the present invention, the energy-application element takes the form of a resistive heating coil to thereby impart heat that radiates toward the coupling, which is a heat-activated coupling when the resistive heating coil is supplied with electrical energy.

In accordance with still another embodiment or aspect of the present invention, the vascular occlusion coil deployment system for use in placing an embolic coil at a preselected site within a vessel includes an elongated flexible delivery member having a lumen extending therethrough. An elongated flexible detachment member is slidably positioned within the lumen of the delivery member. A heating element is affixed to the distal end of the detachment member, and a heat activated coupling member connects the proximal end component of embolic coil to the distal end of the delivery member. The heating element is adapted to be coupled to a source of energy through an energy transmission conductor. The energy transmission conductor extends from the proximal end to the distal end of the detachment member within the lumen of the delivery member and is coupled to the heating element. The heat activated coupling member severs upon being heated by heat energy radiating from the heating element when energy is applied through the conductor to the heating element, to thereby release the embolic coil at a preselected site.

In accordance with still another aspect or embodiment of the present invention, the energy transmission conductor takes the form of two electrical conductors which extend through the lumen of the delivery member and connect to a resistive heating coil at a distal end of a detachment member for applying electrical energy to the coil to thereby cause the coil to become heated.

In accordance with still another aspect or embodiment of the present invention, an embolic coil deployment system is used to deploy an embolic coil at a desired location within the neurovasculature of a patient. After an elongated flexible catheter such as a guiding catheter is in position for access to the target location within the neurovasculature, the development system is positioned therewithin. An elongated flexible delivery member having an embolic coil at its distal end is deployed through the catheter, and a detachment member having an energy-application element at its distal end is located within the lumen of the delivery member. The delivery member is manipulated by the medical professional until the coil is at the desired placement location. Next, the detachment member is slid distally until a marker thereon aligns in a predetermined manner with a marker of the delivery member, at which time the energy-application element is in severing alignment with an energy-activated coupling joining the embolic coil to the delivery member. Energy application radiates to the coupling, rapidly severing the coupling and releasing the embolic coil at the desired placement location With its function completed, the energy-application element and the detachment member to which it is joined are ready to be retracted into the delivery member in a proximal direction, and both the delivery member and the detachment member are removed, singly or together, from the vasculature by proximal direction movement.

In accordance with still another aspect or embodiment of the present invention, the energy-activated coupling member is comprised of a thermoplastic material such as a polymer tube. Other suitable materials include polymers having a chain orientation that causes the polymer to break when heated, or low melting temperature metals and metal alloys such as magnesium and magnesium-containing alloys. The energy-activated coupling member has a relatively low melting point which is above body temperature. Typically, the operating range of a heat-activated coupling member is between about 35 and about 80° C.

Other aspects, objects and advantages of the present invention will be understood from the following description according to the preferred embodiments of the present invention, specifically including stated and unstated combinations of the various features which are described herein, relevant information concerning which is shown in the accompanying drawings.

BRIEF DESCRIPTION OF THE DRAWINGS

In describing the preferred embodiments of the present invention, reference will be made to the accompanying drawings, wherein.

DESCRIPTION OF ILLUSTRATED EMBODIMENTS

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

Figure 1:
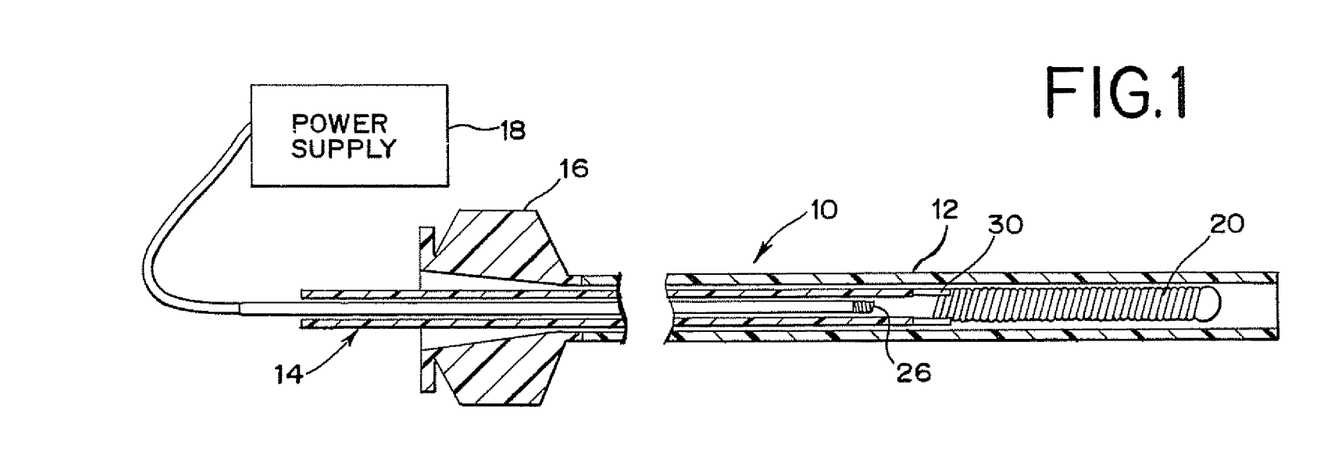
FIG. 1 is an enlarged, partially sectioned view of the vascular occlusion coil deployment system of the present invention in its in-use environment.

FIG. 1 generally illustrates an embodiment of a vascular occlusion coil deployment system of the present invention, generally designated at 10, which is illustrated in combination with an elongated flexible catheter 12 that is utilized to position a coil deployment mechanism, generally designated at 14. A Luer connector 16 is illustrated as a typical connection for the proximal end of the catheter 12, and the coil deployment mechanism 14 is connected to a power supply 18 for applying energy to the coil deployment mechanism 14.

The coil deployment system typically is used for rapidly detaching an embolic coil at a predetermined site within a human body. The illustrated system includes a delivery member having proximal and distal ends and a through lumen. The delivery member additionally includes markers, which typically are radiopaque, affixed proximal to the delivery member distal end. Located near the distal end of the delivery member is an energy-activated, typically heat-activated, coupling that connects the distal end of the delivery member to the proximal end of the embolic coil. The coupling is illustrated formed from a polymer tube having a lumen and proximal and distal portions that are connected to the delivery member and coil, respectively.

Within the delivery member lumen, an elongated detachment member is positioned, such having a shaft with proximal and distal ends and an energy-application element, typically a heating element, disposed at the distal end of the shaft. Conductors such as electrical wires extend from the heating element to the proximal end of the shaft. The entire detachment member is slidably disposed within the lumen of the delivery member. Also included on the shaft of the detachment member are radiopaque markers that when aligned with the markers on the delivery member, places the energy-application element at a position adjacent to the energy-activated or heat-activated coupling member.

Figure 2:
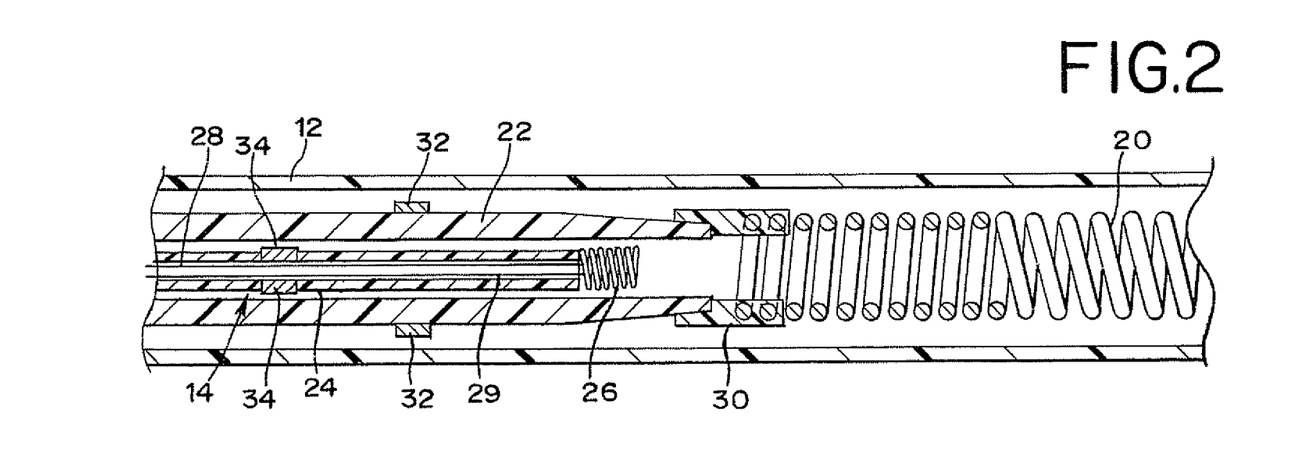
FIG. 2 is an enlarged partially sectioned view showing the coil deployment system placed within a catheter.

FIG. 2 illustrates in more detail the construction of the coil deployment mechanism 14 of this illustrated embodiment. More particularly, the deployment mechanism 14 includes an elongated delivery member 22 which is approximately the same length as the outer catheter 12 and which is slidably received by the catheter 12 in this illustrated embodiment. Delivery member 22 has a lumen extending from its proximal end to its distal end. Coil deployment mechanism 14 also includes a tubular detachment member 24 which is slidably positioned within the lumen of elongated delivery member 22. An energy-applying component which is located at the distal end of the detachment member 24 in this illustrated arrangement is a heating element 26. The delivery member 22 is bonded to the embolic coil 20 by a heat-responsive coupling member 30.

A radiopaque marker 32 is positioned along the elongated delivery member 22. Two or more such markers can be provided at a convenient location that is selected for later coordinating positioning as discussed herein. This selected location is proximal of the distal end of the delivery member 22. A radiopaque marker 34 is positioned along the tubular detachment member 24. Two or more such markers can be provided at a convenient location that is predetermined for later coordination positioning with the selected location of marker 32.

The predetermined location of marker 34, illustrated at a location proximal of the energy-application member, aligns with the selected location of marker 32 when the detachment operation is to begin. In the arrangement shown in the drawings, respective markers 32, 34 radially line up with each other at the position at which the energy-application member 26 is radially aligned with the coupling member 30. In effect, the spacing length between marker 32 and coupling member 30 approximates the spacing length between the marker 34 and the energy-application member or element 26.

Typically, the concept of alignment in this regard indicates that a marker 32 directly overlies a marker 34 such that paired markers 32, 34 merge visually under fluoroscopic or other viewing technology. Likewise, the collar 30, overlies the element 26 when they are in alignment. Alignment need not be strictly limited to direct end-to-end radial coincidence but can be otherwise oriented so the visual message of achieving desired alignment is given to the medical professional. For example, the relative orientation can be such that a narrow gap or slit remains between respective markers 32, 34 when desired alignment is achieved. Also, when multiple marker pairs are used, each pair 32, 34 is to be in alignment as discussed herein, but another pair need not be in radial alignment or in direct end-to-end alignment with the first pair.

The energy-activated coupling member 30 is made of a biocompatible material and may be made of suitable biostable and/or bioabsorbable material that is substantially non-flowing at body temperature The material also may be free-flowing or flows under some applied load. Typical materials have a relatively low melting point so as to be softenable at temperatures not so high as to damage living vessels. In any event the material will have a softening point or a glass transition temperature above body temperature, with a melting point above body temperature. Suitable materials include polymers with polymer chain orientation that causes the polymer to break when heated Examples of suitable biostable materials are polymers, typically thermoplastic polymers such as polyolefins and polyurethanes and most other biocompatible polymers. Typical suitable bioabsorbable materials include polyglycolide (PGA), poly(L-lactide) (PLLA), poly($\epsilon$-caprolactone) (PCL), and blends or combinations thereof. Polyglycolide for example has a glass transition temperature between 35-40° C., such having a considerably higher melting point.

Upon being heated, the biocompatible energy-activated coupling member 30 softens so that it may be severed. The material is to be softened enough by the energy application so as to either melt the material or soften it enough to cause separation when the elongated delivery member 22 is removed (typically along with or in addition to the detachment member 24) from the body, leaving the embolic coil 20 in place within the blood vessel or the like.

The energy applied at the energy-application member 26 typically imparts heat and a resulting elevated temperature to the biocompatible energy-activated coupling member 30. A suitable elevated temperature in this context correlates to the temperature required to soften the material out of which the coupling member 30 is made. As used herein, the temperature of the energy-application member 26 is considered also to approximate temperature to which the coupling member 30 is elevated to during use of the invention. These are at times referred to as operating temperatures.

Typical operating temperatures in this regard are on the order of between about 35 and 80° C., often between about 40 and 60° C. A temperature higher than 80° C. may be suitable for a short period of time and be adequate to cause activation of the coupling member. Any temperature to which the energy-application member and the coupling member is elevated is limited by what the body of the patient can handle without causing damage to the vessel wall or causing thrombus to form. For this reason, it often can be desirable to remain within the temperature ranges illustrated above.

Also, as illustrated in FIG. 2, the energy-application member 26, such as a heating element, is preferably a resistively heated coil coupled to a pair of energy transmission conductors 28, 29. For example, the energy transmission conductors 28, 29 are electrical conductors also coupled to power supply 18. Upon application of an electrical current to the pair of conductors 28, 29, the illustrated heating element begins to heat to thereby cause the energy-activated or heat-responsive coupling member 30 to increase in temperature. As seen in FIGS. 2-6, the coupling member 30 is tubular and has an inside annular surface. The proximal end portion of coupling member tube 30 is attached to the elongated delivery member 22, and the remainder of the inside annular surface of the coupling member tube 30 is an internal annular section is attached to neither the delivery member 22 nor the embolic coil 20. As the coupling member 30 becomes warm, it softens and has a lowered yield strength, thus breaking when the delivery member 24 is retracted to release the embolic coil 20.

Figure 3:
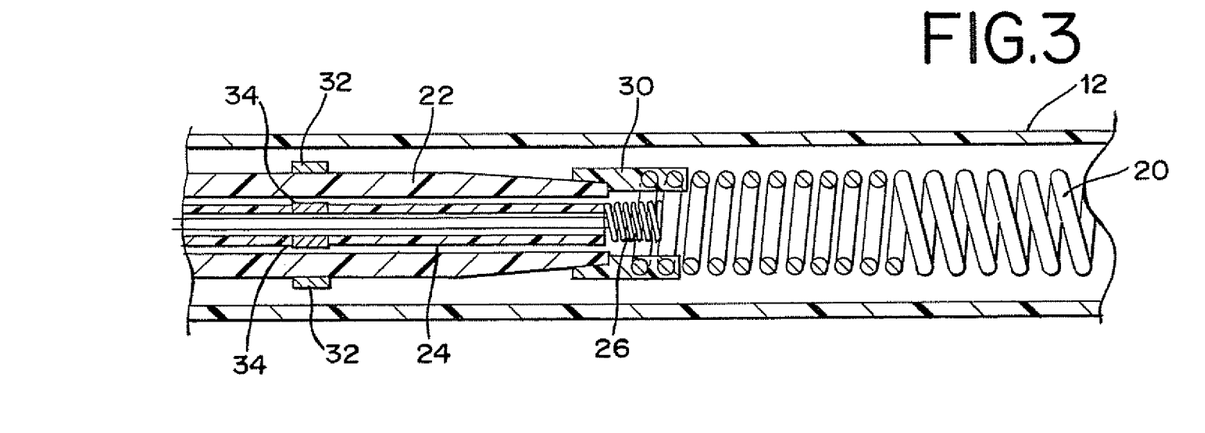
FIG. 3 is an enlarged partially sectioned view illustrating a sequential step of positioning the system in preparation for development of the embolic coil at a preselected site.
Figure 4:
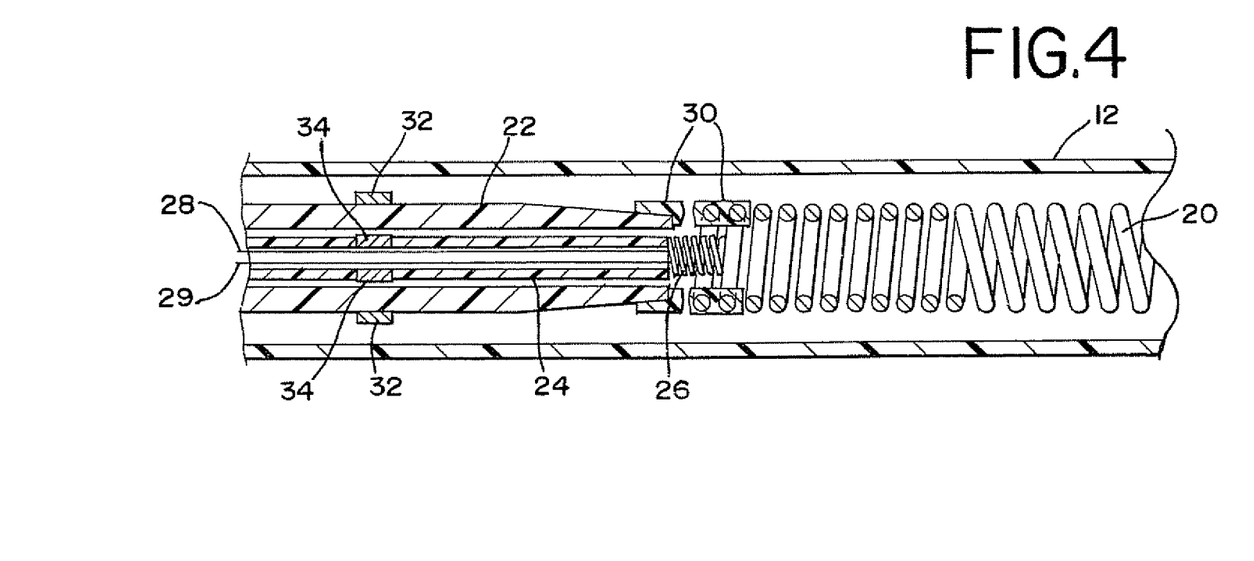
FIG. 4 is an enlarged partially sectioned view illustrating a subsequent sequential step culminating in release of the embolic coil.

More particularly, and as illustrated in FIGS. 2 through 4, the vascular occlusion coil deployment system 10 is inserted into the body, such as into a blood vessel (not shown) and is moved to a position within the blood vessel where it is desirable to place the embolic coil 20. When the catheter 12 has been positioned at a location slightly proximal of the preselected site for placement of the embolic coil, the coil deployment mechanism 14 is pushed out of the distal end of the catheter 12, and the detachment member and its element 26 are properly positioned, and electrical energy is then applied to the element 26 to thereby soften the coupling member 30 that now is in close proximity thereto.

Once the coupling member 30 softens, the delivery member 22 is retracted, thus disengaging the delivery member from embolic coil 20, breaking the integrity of the coupling member 30. As the delivery member 22 is retracted, there is no longer engagement between the delivery member 22 and the embolic coil 20, and the coil is released to the selected location within the body vessel. Finally, the coil deployment mechanism 14 is withdrawn back into the catheter 12 and the embolic coil 20 remains in its deployed position.

With the vascular occlusion coil deployment system of the present invention it is possible to place an embolic coil very precisely at a desired location within a vessel. Once the coil has been placed in a preselected location by catheter, the deployment mechanism may be activated by applying energy to a coil release mechanism to thereby cause the coil to be released and deposited at a desired location.

As an example of operation of the coil deployment system, a physician navigates a catheter within the vasculature of a patient to a position adjacent a target site. Once the catheter has been properly positioned, the coil-mounted delivery member is advanced through the catheter. The coil then exits the catheter and may be properly positioned at the target site. Once the coil is positioned, the detachment member is advanced through the delivery member such that the marker or markers on the detachment member align fluoroscopically with the marker or markers on the delivery member. This positions the heating element adjacent to the heat-activated coupling. Energy, typically electrical, then is supplied to the heating element causing it to heat and elevate in temperature, thus activating the heat-activated coupling to thereby cause the coupling to release the embolic coil, as shown in FIG. 4. After release of the coil, the delivery and detachment members may be withdrawn from the patient.

Figure 5:
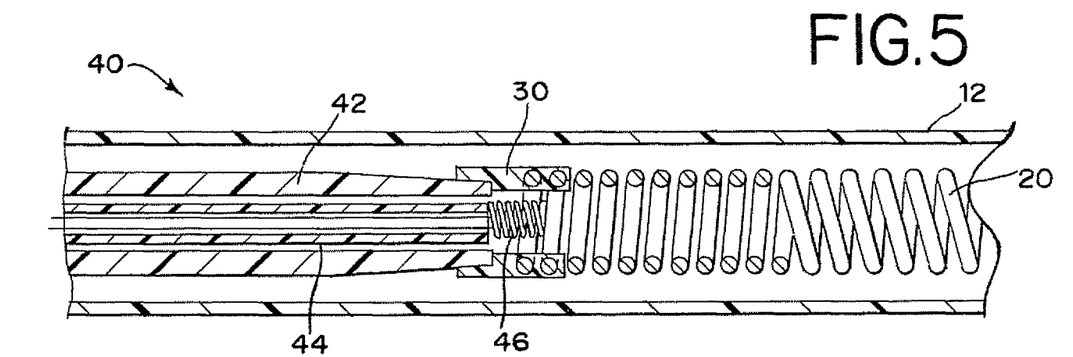
FIG. 5 is an enlarged partially sectioned view illustrating another embodiment of the vascular occlusion coil deployment system.
Figure 6:
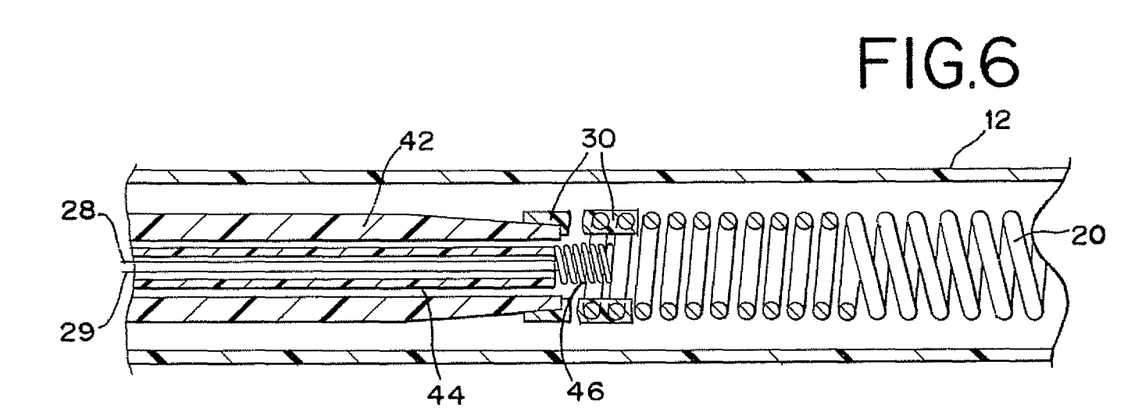
FIG. 6 is an enlarged partially sectioned view illustrating release of the embolic coil according to the embodiment of FIG. 5.

With reference to the embodiment of FIGS. 5 and 6, this vascular occlusion coil deployment system contains the elongated flexible catheter 12 for positioning a coil deployment mechanism, generally designated at 40. This deployment mechanism 40 includes an elongated delivery member 42 which is approximately the same length as the outer catheter 12 and which is slidably received by the catheter 12. Delivery member 42 has a lumen extending from its proximal end to its distal end. Coil deployment mechanism 40 also includes a tubular detachment member 44 positioned within the lumen of the elongated delivery member 42. An energy-applying component which is located at the distal end of the detachment member 44 in this illustrated arrangement is a heating element 46. The embolic coil 20 is bonded to the elongated delivery member 42 by a heat-responsive coupling member 30.

The energy-active or heat-responsive coupling member 30 is made of materials as discussed herein with respect to other embodiments. This member 30 exhibits softening, melting, breaking and severing properties as discussed herein. The energy-application member 46 is a generally disclosed herein with respect to other embodiments. Once the coupling member 30 is softened by action of the energy-application member 46 thereonto, the delivery member 42 is retracted, there is no longer engagement between the delivery member and the embolic coil 20, and the coil is released to the selected location within the body vessel. Finally, the coil deployment mechanism 40 is withdrawn back into the catheter 12, and the embolic coil 20 remains in its deployed position.

As is apparent, there are numerous modifications of the embodiments described above which will become readily apparent to one skilled in the art, such as many variations and modifications of the deployment system including many different variations of the heating element, many variations of energy sources, such as optical, radiofrequency, and acoustical, many variations of energy transmission conductors such as optical fiber, and many variations of heat softening materials. These include modifications that would be apparent to those having ordinary skill in the art to which this invention relates and are intended to be within the scope of the claims which follow.

It will be understood that the embodiments of the present invention which have been described are illustrative of some of the applications of the principles of the present invention. Numerous modifications may be made by those skilled in the art without departing from the true spirit and scope of the invention, including those combinations of features that are individually disclosed or claimed herein.

The invention claimed is:

1. A vascular occlusion coil deployment system for use in placing a coil at a preselected site within a vessel comprising:
   an elongated flexible delivery member having a lumen extending therethrough and having proximal and distal ends;
   an embolic coil having a proximal portion;
   a heat-activated coupling member that is a biocompatible polymer tube joining said embolic coil to the distal end of the delivery member, said coupling member tube being coaxial with the delivery member and having a proximal end portion that is attached to the distal end of the elongated flexible delivery member, said coupling member tube having a distal end portion that is bonded to the proximal portion of the embolic coil, and said coupling member tube having an internal annular section that is attached to neither the delivery member nor the embolic coil;

said internal annular section of the coupling member tube is coaxial with the delivery member and the coupling member is of substantially uniform thickness throughout;

an elongated flexible detachment member having a lumen extending therethrough, the detachment member being coaxial with the delivery member and slidably positioned within the lumen of the delivery member and having proximal and distal ends;

a heating element mounted on the distal end of the detachment member, said heating element being an electrically heated coil that is unattached to the elongated delivery member, is unattached to the coupling member tube while the embolic coil is fixedly attached to the delivery member, and is slidably positioned within the delivery member and within the coupling member tube;

a marker at a selected location proximal of the distal end of the delivery member;

another marker at a predetermined location proximal of the distal end of the detachment member, said marker predetermined location aligns with said selected location of the marker of the delivery Member when said heating element aligns with said internal annular section of the coupling member tube of the delivery member; and said internal annular section of the coupling member tube softens in response to heat radiating from said thereby aligned heating element and, upon being so heated, breaks when said delivery member is retracted with respect to said coil to release said embolic coil and movement of said delivery member severs the internal annular section of the coupling member tube to release said embolic coil.

2. The vascular occlusion coil deployment system as defined in claim 1, said biocompatible polymer coupling member tube being substantially non-flowing at body temperature and flows in response to heat energy from said heating element.

3. The vascular occlusion coil deployment system as defined in claim 1, wherein said coupling member tube softens in response to a temperature of said heating element of between about 35 and 80° C. and above.

4. The vascular occlusion coil deployment system as defined in claim 1, wherein said coupling member tube softens in response to an operating temperature of between about 40 and about 60° C.

5. The vascular occlusion coil deployment system as defined in claim 1, wherein said coupling member tube biocompatible polymer is selected from a biostable polymer and a bioabsorbable polymer.

6. The vascular occlusion coil deployment system as defined in claim 1, further including a non-optical energy transmission conductor extending along a lumen of the detachment member and extending from the proximal end to the distal end of the detachment member, said energy transmission conductor being coupled to said heating element.

7. The vascular occlusion coil deployment system as defined in claim 1, wherein said marker at a selected location and said marker at a predetermined location comprise a pair of markers, and further comprising at least two said pairs of markers.

8. The vascular occlusion coil deployment system as defined in claim 1, wherein said delivery member marker at a selected location is in end-to-end radial alignment with said detachment member marker at a predetermined location.

9. The vascular occlusion coil deployment system as defined in claim 7, wherein said pairs of markers are in end-to-end radial alignment with each other.

10. A vascular occlusion coil deployment system for use in placing a coil at a preselected site within a vessel comprising:

an elongated flexible delivery member having a lumen extending therethrough and having proximal and distal ends;

an embolic coil having a proximal portion;

an energy-activated coupling member that is a biocompatible polymer tube joining said embolic coil to the distal end of the delivery member, said coupling member being a tube coaxial with the delivery member, said coupling member tube being a biocompatible polymer that is substantially non-flowing at body temperature and flows in response to energy applied thereto, said coupling member tube having a proximal end portion that is attached to the distal end of the elongated flexible delivery member, said coupling member tube having a distal end portion that is bonded to the proximal portion of the embolic coil, and said coupling member tube having an internal annular section that is attached to neither the delivery member nor the embolic coil;

said internal annular section of the coupling member tube is coaxial with the delivery member and the coupling member, is un-scored, and is of substantially uniform thickness throughout;

an elongated flexible detachment member having a lumen extending therethrough, being coaxial with the delivery member and being slidably positioned within the lumen of the delivery member and having proximal and distal ends;

an energy-responsive element mounted on the distal end of the detachment member, said energy-responsive element being in communication with a source of energy, and said energy-responsive element is unattached to the elongated delivery member, is unattached to the coupling member tube while the embolic coil is fixedly attached to the delivery member, and is slidably positioned within the delivery member and within the coupling member tube;

a radiopaque marker at a selected location proximal of the distal end of the delivery member;

another radiopaque marker at a predetermined location proximal of the distal end of the detachment member, said marker predetermined location aligns with said selected location of the marker of the delivery member when said energy-responsive element aligns with said internal annular section of the coupling member of the delivery member; and said internal annular section of the coupling member softens in response to energy radiating from said energy-responsive element thereby aligned with said internal annular section of the coupling member and, upon being so softened, breaks when said delivery member is retracted with respect to said coil to release said embolic coil and movement of said delivery member severs the internal annular section of the coupling member to release said embolic coil.

11. The vascular occlusion coil deployment system as defined in claim 10, wherein said coupling member comprises a polymer that softens in response to an operating temperature of said energy-responsive element of between about 35 and 80° C. and above.

12. The vascular occlusion coil deployment system as defined in claim 10, wherein said marker at a selected location and said marker at a predetermined location comprise a pair of markers, and further comprising at least two said pairs of markers.

13. The vascular occlusion coil deployment system as defined in claim 10, wherein said delivery member marker at a selected location is in end-to-end radial alignment with said detachment member marker at a predetermined location.

14. The vascular occlusion coil deployment system as defined in claim 12, wherein said pairs of markers are in end-to-end radial alignment with each other.

15. A method for deploying a vascular occlusion coil at a preselected site within a vessel comprising:

providing a coil deployment system including an elongated flexible delivery member having a lumen extending therethrough, an embolic coil, a heat-activated coupling member that is a biocompatible polymer tube bonding a distal end portion of the coupling member tube to the embolic coil and joining a proximal end portion of the coupling member tube to the distal end of the delivery member, with a substantially uniform thickness internal annular section of the coupling member tube being between the proximal and distal end portions thereof, an elongated flexible detachment member positioned within the lumen of the delivery member, a heating element mounted on the distal end of the detachment member, wherein the heating element is unattached to the elongated delivery member, is unattached to the coupling member tube while the embolic coil is fixedly attached to the delivery member, and is slidably positioned within the delivery member and within the coupling member tube a radiopaque marker at a selected location proximal of the distal end of the delivery member, and another marker at a predetermined location proximal of the distal end of the detachment member;

said providing including longitudinally spacing the marker on the delivery member at a selected distance from the coupling member tube;

said providing further including longitudinally spacing the marker on the detachment member at a predetermined distance from the heating element, the selected distance being substantially equal to the predetermined distance;

sliding the detachment member with respect to the delivery member until the markers align with each other and thereby automatically aligning the heating element with the internal annular section of the coupling member tube;

applying energy to the heating element to thereby soften the internal annular section of the coupling member tube in response to heat radiating from the heating element, and thereafter moving the elongated flexible delivery member in a proximal direction in order to thereby separate the embolic coil from the delivery member; and withdrawing the coil deployment system from the body, while leaving the embolic coil in place.

16. The method of claim 15, wherein said applying energy heats the coupling member to an operating temperature of between about 35 and 80° C. and above.

17. The method of claim 15, wherein said applying energy and thereafter moving the delivery member combine to break the internal annular section of the coupling member tube to remove the embolic coil from the coil deployment system.

18. A vascular occlusion coil deployment system for use in placing a coil at a preselected site within a vessel comprising:

an elongated flexible delivery member having a lumen extending therethrough and having proximal and distal ends;

an embolic coil having a proximal portion;

a heat-activated coupling member tube joining said embolic coil to the distal end of the delivery member, said coupling member tube being a biocompatible polymer material that is substantially non-flowing at body temperature and flows in response to energy applied thereto, said coupling member tube having a proximal end portion that is attached to the distal end of the elongated flexible delivery member, said coupling member tube having a distal end portion that is bonded to the proximal portion of the embolic coil, and said coupling member tube having an internal annular section that is attached to neither the delivery member nor the embolic coil;

said internal annular section of the coupling member tube is coaxial with the delivery member and the coupling member is of substantially uniform thickness throughout;

an elongated flexible detachment member having a lumen extending therethrough and being slidably positioned within the lumen of the delivery member and having proximal and distal ends;

a heat-application element mounted on the distal end of the detachment member, said heat-application element being in communication with a source of energy, and said heat-application element is unattached to the elongated delivery member, is unattached to the coupling member tube while the embolic coil is fixedly attached to the delivery member, and is slidably positioned within the delivery member and within the coupling member tube; and said internal annular section of the coupling member tube softens in response to heat radiating from said heat-application element thereby aligned with said internal annular section of the coupling member tube, thereby allowing breaking of the internal annular section of the coupling member tube and releasing of the embolic coil from the delivery member.

19. The vascular occlusion coil deployment system as defined in claim 18, wherein said coupling member tube polymer softens in response to a temperature of said heating element of between about 35 and 80° C. and above.

20. The vascular occlusion coil deployment system as defined in claim 18, wherein said coupling member tube polymer softens in response to an operating temperature of between about 40 and about 60° C.

21. The vascular occlusion coil deployment system as defined in claim 18, wherein said biocompatible polymer is selected from a biostable polymer and a bioabsorbable polymer.

22. The vascular occlusion coil deployment system as defined in claim 18, wherein said internal annular section of the heat-activated coupling member, upon being heated, breaks when said delivery member is retracted with respect to said coil to release said embolic coil and wherein the release of said embolic coil comprises softening of said internal annular section of the coupling member by heat from said heating element, and movement of said delivery member severs the internal annular section of the coupling member to release said embolic coil.

* * * * *